US005750495A

United States Patent [19]
Woo

[11] Patent Number: 5,750,495
[45] Date of Patent: May 12, 1998

[54] TREATMENT OF CYSTIC DISEASE WITH TNF-α

[75] Inventor: David D. L. Woo, Los Angeles, Calif.

[73] Assignee: The Regents of the University of California, Oakland, Calif.

[21] Appl. No.: 621,629

[22] Filed: Mar. 26, 1996

[51] Int. Cl.$^6$ .......................... A61K 38/00; A01N 37/18
[52] U.S. Cl. ............................................... 514/2; 514/642
[58] Field of Search .................................... 514/642, 2

[56] References Cited

FOREIGN PATENT DOCUMENTS

WO 94/08041   4/1994   WIPO.

OTHER PUBLICATIONS

Woo et al., "Taxol inhibits progression of congenital polycystic kidney disease", Nature, vol. 368, Apr. 21, 1994, pp. 750–753.

T. Akimoto, et al. (1994) "Antitumor Effect of DT-5641a, a Synthetic Low–Toxicity Lipid a Analog, Involves Endogenous Tumor Necrosis Factor Induction Subsequent to Macrophage Activation", Int. J. Immunopharmac., 16(11):887–893.

E.D. Avner, et al. (1992) "Abnormal Sodium Pump Distribution During Renal Tubulogenesis in Congenital Murine Polycystic Kidney Disease", Proc. Natl. Acad. Sci. U.S.A., 89:7447–7451.

B. Beutler, et al. (1994) "Unraveling Function in the TNF Ligand and Receptor Families", Science 264:667–668.

A.P. Bollon, et al. (1988) "Human Cytokines, Tumor Necrosis Factor, and Interferons: Gene Cloning, Animal Studies, and Clinical Trials", Journal of Cellular Biochemistry, 36:353–367.

E.A. Carswell, et al. (1975) "An Endotoxin–Induced Serum Factor that Causes Necrosis of Tumors", Proc. Nat. Acad. Sci. U.S.A., 72(9):3666–3670.

B.D. Cowley, et al. (1991) "Elevated Proto–Oncogene Expression in Polycystic Kidneys of the C57BL/6J (CPK) Mouse", J. Am. Soc. Nephrol., 1:1048–1053.

M.C. Daoust, et al. (1995) "Evidence for a Third Genetic Locus for Autosomal Dominant Polycystic Kidney Disease", Genomics, 25:733–736.

M.T. Davisson, et al. (1991) "The Mouse Polycystic Kidney Disease Mutation (cpk) is Located on Proximal Chromosome 12", Genomics, 9:778–781.

I. Ebihara, et al. (1988) "Altered mRNA Expression of Basement Membrane Components in a Murine Model of Polycystic Kidney Disease", Laboratory Investigation, 58(3):262–269.

V.H. Gattone II, et al. (1991) "Murine Infantile Polycystic Kidney Disease: A Role for Reduced Renal Epidermal-growth Factor", American Jour. of Kidney Diseases, XVII(6):606–607.

S. Golding, et al. (1995) "Tenidap–Modulated Proinflammatory Cytokine Activation of a Monocyte Cell Line", The Journal of Immunology, 154:5384–5390.

D.E. Griswold, et al. (1993) "Differentiation In Vivo of Classical Non–Steroidal Antiinflammatory Drugs from Cytokine Suppressive Antiinflammatory Drugs and Other Pharmacological Classes Using Mouse Tumour Necrosis Factor Alpha Production", Drugs Exptl. Clin. Res., XIX(6):243–248.

M.A. Harding, et al. (1991) "The SGP–2 Gene is Developmentally Regulated in the Mouse Kidney and Abnormally Expressed in Collecting Duct Cysts in Polycystic Kidney Disease", Devel. Biol. 146:483–490.

S. Horikoshi, et al. (1991) "Epidermal Growth Factor (EGF) Expression in the Congenital Polycystic Mouse Kidney", Kidney International, 39:57–62.

W.J. Kimberling, et al. (1993) "Autosomal Dominant Polycystic Kidney Disease: Localization of the Second Gene to Chromosome 4q13–q23", Genomics, 18:467–472.

J. Mandell, M.D., et al. (1993) "Animal Model of Human Disease: Congenital Polycystic Kidney Disease", Am. J. Pathol., 113(1):112–114.

D.F. Mangan, et al. (1991) "Lipopolysaccharide, Tumor Necrosis Factor–α, and II–1β Prevent Programmed Cell Death (Apoptosis) in Human Peripheral Blood Monocytes[1]", The Journal of Immunology, 146:1541–1546.

R.A. McDonald, et al. (1991) "Inherited Polycystic Kidney Disease in Children", Seminars in Nephrology, 11(6):632–642.

S.A. Orellana, et al. (1995) "Epidermal Growth Factor Receptor Expression is Abnormal in Murine Polycystic Kidney", Kidney International, 47:490–499.

G.M. Preminger, M.D., et al. (1982) "Murine Congenital Polycystic Kidney Disease: A Model for Studying Development of Cystic Disease", The Journal of Urology, 127:556–560.

S.T. Reeders, et al. (1985) "A Highly Polymorphic DNA Marker Linked to Adult Polycystic Kidney Disease on Chromosome 16", Nature, 317:542–544.

M.J. Reiter, et al. (1994) "Cytokine Induction in Mice by the Immunomodulator Imiquimod", Journal of Leukocyte Biology, 55:234–240.

M. Taub, et al. (1990) "Altered Basement Membrane Protein Bosynthesis by Primary Cultures of CPK/CPK Mouse Kidney", Kidney International, 37:1090–1097.

M. Tsujimoto, et al. (1985) "Tumor Necrosis Factor: Specific Binding and Internalization in Sensitive and Resistant Cells", Proc. Natl. Acad. Sci. U.S.A.82:7626–7630.

(List continued on next page.)

Primary Examiner—Marianne M. Cintins
Assistant Examiner—Dwayne C. Jones
Attorney, Agent, or Firm—Knobbe, Martens, Olson & Bear, LLP

[57] ABSTRACT

A method for treating polycystic kidney disease in an individual in need thereof. This method includes identifying a mammal having a cystic disease and administering to the mammal a pharmacologically effective anti-cystic amount of TNF-α or an agent which stimulates TNF-α production in vivo. The agent is administered in a pharmacologically acceptable carrier, excipient or diluent.

6 Claims, 2 Drawing Sheets

OTHER PUBLICATIONS

B.B. Warner, et al. (1991) "Tumor Necrosis Factor-α Increases Mn-SOD Expression: Protection Against Oxidant Injury", *The American Physiological Society*, L296-L301.

G.H.W. Wong, et al. (1988) "Induction of Manganous Superoxide Dismutase by Tumor Necrosis Factor: Possible Protective Mechanism", *Science*, 242:941-944.

D.D.L. Woo, et al. (1994) "Taxol Inhibits Progression of Congenital Polycystic Kidney Disease", *Nature*, 368:750-753.

D. Woo, Ph.D. (1995) "Apoptosis and Loss of Renal Tissue in Polycystic Kidney Diseases", *The New England Journal Of Medicine*, 333(1):18-25.

K. Zerres, et al. (1994) "Mapping of the Gene for Autosomal Recessive Polycystic Kidney Disease (ARPKD) to Chromosome 6p21-cen", *Nature Genetics*, 7:429-432.

TREATMENT OF CYSTIC DISEASE WITH TNF-α

STATEMENT OF GOVERNMENT SUPPORT

This invention was made with United States government funding under NIH Grant No. DK 40700. The government may have certain rights in the invention.

FIELD OF THE INVENTION

The present invention relates to treatment of cystic diseases. More specifically, the invention relates to treatment of polycystic kidney disease by administration of TNF-α or agents which stimulate production of TNF-α.

BACKGROUND OF THE INVENTION

There are many human diseases which result in the formation of cysts which contain either semi-solid or fluid material. The contents of a cyst sometimes drive from normally retained fluid (e.g. a sebaceous cyst can contain fluid from a blocked sebaceous gland) or from a parasitic infection. Benign cysts can occur in the ovary, spleen, lungs, kidney and liver, where they are often congenital. Some congenital cysts result from fetal malformations and developmental failure while others are directs results of a disease state.

The polycystic kidney diseases (PKD) are a group of disorders characterized by the presence of a large number of fluid-filled cysts throughout grossly enlarged kidneys (Gabow et al., Diseases of the Kidney, Schrier et al. eds., 1992). In humans, PKDs can be inherited in autosomal dominant (ADPKD) or autosomal recessive (ARPKD) forms. ADPKD is the most common, dominantly-inherited kidney disease in humans, occurring at a frequency of about 1 in 800. ARPKD occurs at a frequency of about 1 in 10,000. Clinically, PKD represents a major cause of end-stage renal disease. Microdissection, histochemical and immunologic studies show that cysts in ARPKD kidneys arise from focal dilations of medullary collecting ducts (McDonald, Semin. Nephrol., 11:632–642, 1991). Mutations in at least three different loci have been associated with ADPKD in humans, including PKD1 on chromosome 16, PKD2 on chromosome 4, and the not yet mapped PKD3 (Reeders et al., Nature, 317:542–544, 1985; Kimberling et al., Genomics, 18:467–472, 1993; Daoust et al., Genomics, 25:733–736, 1995). The ARPKD mutation is on human chromosome 6 (Zerres et al., Nature Genet., 7:429–432, 1994). The molecular mechanisms leading to cyst enlargement and progressive loss of renal function in PKDs are not completely understood. Besides dialysis and transplantation, which are palliative, there are no preventive or curative treatment for PKDs.

In 1977, it was reported that a recessive congenital polycystic kidney (cpk) disease arose spontaneously in C57BL/6J mice (Preminger et al., J. Urol., 127:556–560, 1982). The cpk mutation has been mapped to mouse chromosome 12 (Davisson et al., Genomics, 9:778–781, 1991). Kidney maldevelopment and progression of PKD in C57BL/6-cpk/cpk mice have been characterized in detail (Preminger, ibid.; Mandell et al., Am. J. Pathol., 113:112–114, 1983). Affected animals appear normal at birth and have microscopic dilations of their proximal renal tubules. These enlarged tubules develop into cysts. At 10–13 days of age, homozygous cpk/cpk animals may be recognized by protuberant abdomens resulting from greatly enlarged kidneys. After day 10–12, additional cysts develop rapidly from dilations of medullary collecting ducts. Consequently, the kidneys rapidly enlarge, reaching almost 2.0 g in kidney weight at day 24 compared to about 0.18 g for age-matched normal kidneys. Cystic expansion is accompanied by the apoptotic loss of non-cystic nephrons (Woo, New Engl. J. Med., 333:18–25, 1995). Concomitant with kidney enlargement, there is a gradual decrease in kidney function with blood urea nitrogen (BUN) reaching 120 mg/dL by 24 days of age. Polycystic mice become progressively lethargic and die by 28–35 days of age due to renal failure.

Hallmark features of cystic changes in human PKD epithelia such as cellular hyperplasia and abnormal basement membrane are observed in cpk cysts at both the light and electron microscopic level (Gattone et al., Am. J. Kidney Dis., 17:606–607, 1991). The accumulation of fluid in cysts indicates abnormal fluid transport in cpk cystic epithelia. The presence of altered expression of basement membrane (Taub et al., Kidney Int., 37:1090–1097, 1990; Ebihara et al., Lab. Invest., 58:262–269, 1988), altered growth-controlling gene expression (Horikoshi et al., Kidney Int., 39:57–62, 1991; Gattone et al., Dev. Biol., 138:225–230, 1990; Cowley et al., J. Am. Soc. Nephrol., 1:1048–1053, 1991), altered targeting of the normally basolaterally sodium-potassium ATPase and EGF receptor (Avner et al., Proc. natl. Acad. Sci. U.S.A., 89:7447–7451, 1992; Orellana et al., Kidney Int., 47:490–499, 1995), and expression of developmentally dedifferentiated phenotypes (Harding et al., Dev. Biol., 146:483–490, 1991) make the cpk mouse a useful animal for studying the diverse renal pathobiologies of PKD. The overall progression of PKD is very similar in the cpk mouse and in humans.

The microtubule-specific drug taxol significantly inhibits the progression of PKD and significantly prolongs the survival of polycystic cpk mice (Woo et al., Nature, 368:750–753,1994; PCT WO94/08041). Instead of dying of azotemia by four to five weeks of age, polycystic mice treated weekly with taxol can survive to more than six months of age. Taxol binds to microtubules and inhibits microtubule depolymerization. Accordingly, the microtubule cytoskeleton has been postulated to play a role in pathogenesis of PKD in the cpk mouse. In addition to its microtubule stabilizing effects, taxol specifically induces the expression of tumor necrosis factor-α (TNF-α) in macrophages and lymphocytes. The ability of taxol to induce production of TNF-α is not shared by other members of the taxane family.

TNF-α is a pleiotropic cytokine that mediates diverse cellular responses including cytotoxicity, cytostasis, proliferation, differentiation and the expression of specific genes (Beutler et al., Science, 264:667–668, 1994). TNF-α is cytotoxic for a wide variety of tumor cells, but only toxic to a few selected normal cell types (Carswell et al., Proc. Natl. Acad. Sci. U.S.A., 72:3666–3670, 1975; Tsujimoto et al., Proc. Natl. Acad. Sci. U.S.A., 82:7626–7630, 1985). Despite the presence of cell surface TNF-α receptors, the majority of normal mammalian cells are resistant to the cytotoxic effects of TNF-α (Tsujimoto et al., ibid). In addition, TNF-α is protective against apoptotic cell death in several cell types (Wong et al., Science, 242:941–944, 1988; Mangan et al., J. Immunol., 146:1541–1546, 1991; Warner et al., Am. J. Physiol., 260:L296–L301, 1991).

Thus, there is a need for a therapeutic agent capable of treating cystic disease. The present invention satisfies this need.

SUMMARY OF THE INVENTION

One embodiment of the present invention is a method of treating a mammal having a cystic disease, comprising the step of administering to the mammal a pharmacologically effective anti-cystic amount of TNF-α or an agent which stimulates TNF-α production in vivo, with the proviso that the agent is not taxol, the agent being administered in a pharmacologically acceptable carrier, excipient or diluent. Preferably, the mammal is a human. According to one aspect of this preferred embodiment, the cystic disease is breast cysts, bronchogenic cysts, choledochal cysts, colloidal cysts, congenital cysts, dental cysts, epidermoid inclusions, hepatic cysts, hydatid cysts, lung cysts, mediastinal cysts, ovarian cysts, periapical cysts, pericardial cysts or polycystic kidney disease. Advantageously, the cystic disease comprises a polycystic kidney disease. Preferably, the administering step is intravenous, intraperitoneal or intramuscular.

DETAILED DESCRIPTION OF THE PREFERRED EMBODIMENT

Figure 1:
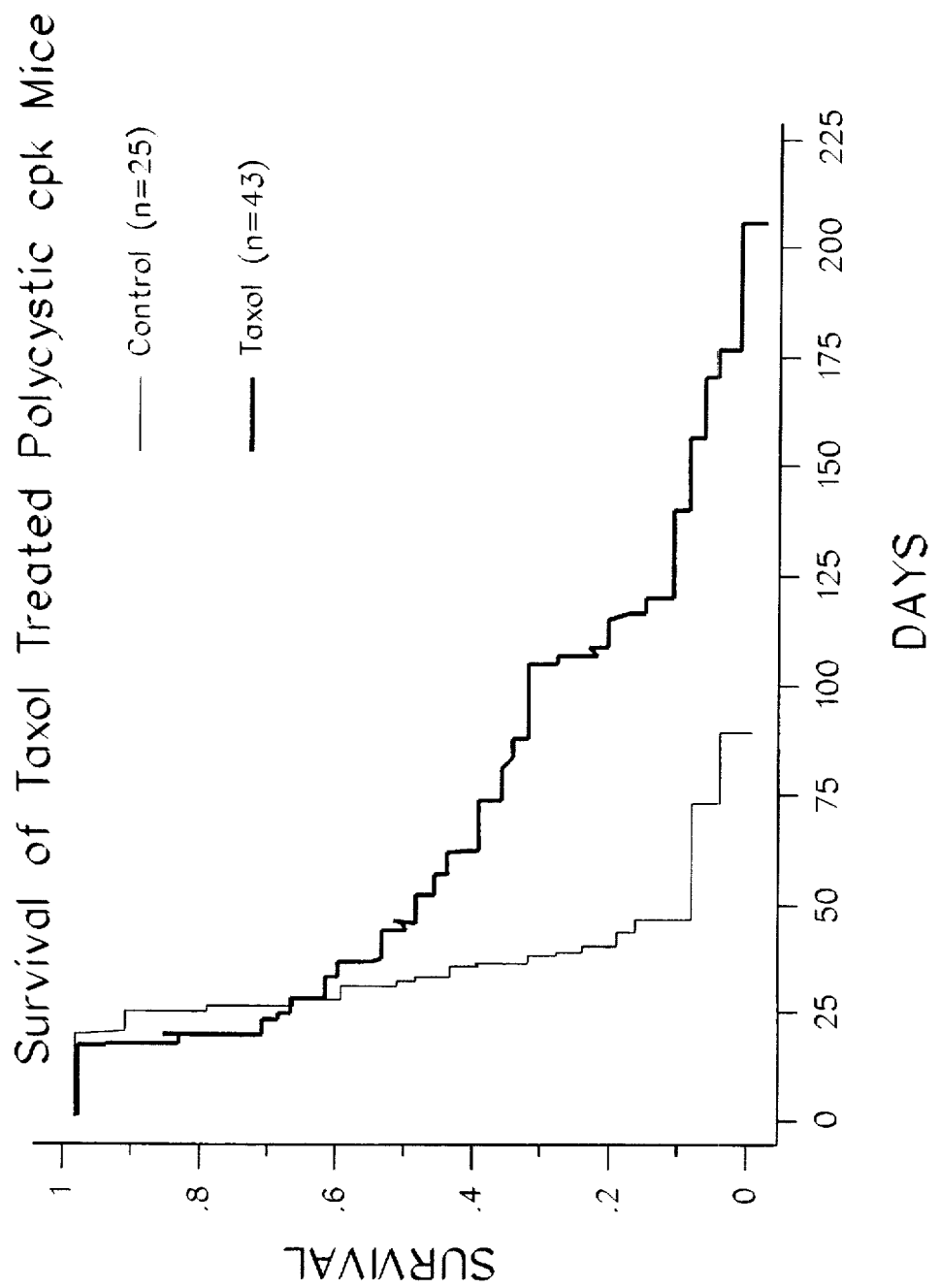
FIG. 1 shows the survival of taxol-treated polycystic cpk mice. The number of days after taxol or placebo treatment is shown on the x-axis and the survival rate is shown on the y-axis.

The present invention provides a method of treating PKD by administration of TNF-α or an agent which stimulates the production of TNF-α. Although the treatment of PKD is exemplified herein, the treatment of any cystic disease is within the scope of the invention. Such cystic diseases include breast cysts, bronchogenic cysts, choledochal cysts, colloidal cysts, congenital cysts, dental cysts, epidermoid inclusions, hepatic cysts, hydatid cysts, lung cysts, mediastinal cysts, ovarian cysts, periapical cysts, pericardial cysts or polycystic kidney disease.

TNF-α or an agent which stimulates TNF-α production may be administered by various routes, including intravenously, intraperitoneally, intramuscularly, intraarterially, subcutaneously, orally or in any other appropriate way known in the art in a pharmaceutically acceptable carrier, excipient or diluent. TNF-α for parenteral administration may be in the form of a sterile injectable preparation, such as a sterile injectable aqueous or oleaginous suspension. This suspension may be formulated according to methods well known in the art using suitable dispersing or wetting agents and suspending agents. The sterile injectable preparation may also be a sterile injectable solution or suspension in a parenterally acceptable diluent or solvent, such as a solution in 1,3-butanediol. Suitable diluents include, for example, water, Ringer's solution and isotonic sodium chloride solution. In addition, sterile fixed oils may be employed conventionally as a solvent or suspending medium. For this purpose, any bland fixed oil may be employed including synthetic mono- or diglycerides. In addition, fatty acids such as oleic acid may likewise be used in the preparation of injectable preparations.

The tolerated dose of recombinant TNF-α in phase I clinical trials is 150,000 units/kg (Bollon et al., *J. Cell. Biochem.*, 36:353–367, 1988). The preferred effective dose range of TNF-α for treatment of human cystic diseases is between about 50,000 units/kg and 150,000 units/kg; a more preferred dose is between about 75,000 units/kg and about 125,000 units/kg; a most preferred dose is about 100,000 units/kg. This treatment is typically repeated every two or three days until a significant improvement in the cystic disease is observed. TNF-α can be administered either before a cyst has formed, to prevent its formation, or after a cyst has already been detected.

In addition, agents which stimulate TNF-α production are also useful in treating cystic diseases. Such agents include, for example, the non-steroidal antiinflammatory drugs indomethacin, naproxen and ibuprofen (*Drugs Exp. Clin. Res.*, 19:243–248, 1993), tenidap (Golding et al., *J. Immunol.*, 154:5384–5390, 1995), a synthetic low-toxicity lipid A analog (Akimoto et al., Int. *J. Immunopharmacol.*, 16:887–893, 1994) and imiquod (*J. Leukoc. Biol.*, 55:234–240, 1994. The ability of such compounds to treat cystic diseases may be determined by one of ordinary skill in the art using the mouse cpk polycystic kidney disease model as described in Example 1 for TNF-α and taxol treatment.

EXAMPLE 1

TNF-α and taxol treatment of cpk mice

Heterozygous C57BL/6-cpk/+ breeder mice were obtained from the Jackson Laboratory (Bar harbor, Me. The cpk mouse colony was maintained by mating known heterozygotes. Mice were kept with their mothers until they were weaned at 28 days of age.

Taxol obtained from the Drug Synthesis and Chemistry Branch of the National Cancer Institute (Bethesda, Md.) was dissolved at 10 mg/ml in dimethyl sulfoxide (DMSO) and stored at −20° C. Taxol treatment was initiated on 10 day old polycystic cpk mice diagnosed to be polycystic by the presence of palpably enlarged kidneys. Mice were injected intraperitoneally with 10 μg of taxol per gram body weight on day 10 and 100 μg taxol per animal on subsequent weeks. Polycystic mice treated with an equal volume of DMSO were used as controls.

Weekly taxol treatment clearly increased the survival rate of cpk mice (n=43) compared to control (carrier vehicle treated mice (FIG. 1). When weekly taxol treatment was initiated at 10 days of age, 60% of all polycystic mice survived past 40 days of age, while at this time, 80% of the untreated polycystic cpk mice had died. 35% of polycystic mice treated weekly with taxol lived past 90 days of age, while all polycystic cpk mice treated with DMSO died. Statistically, the difference in survival between control and taxol treated mice is highly significant (Log-rank chi-square=7.80 and p=0.005). The serum creatinine of three taxol treated polycystic cpk mice when sacrificed at 90 days of age was 2.8±0.8 mg/dL (vs. 6.0 mg/dL in untreated 24 day old mice).

Sterile recombinant murine TNF-α (1 mg/ml, Genentech, South San Francisco, Calif.) was stored at 4° C. in phosphate buffered saline (PBS). Beginning on day 7 after birth, the entire litter of mice from selective matings was injected intraperitoneally with 2 μl TNF-α every other day. After day 10, only mice with palpable polycystic kidneys continued to receive TNF-α. Polycystic mice identically treated with PBS were used as controls. All polycystic mice were continually treated for the duration of their life.

Figure 2:
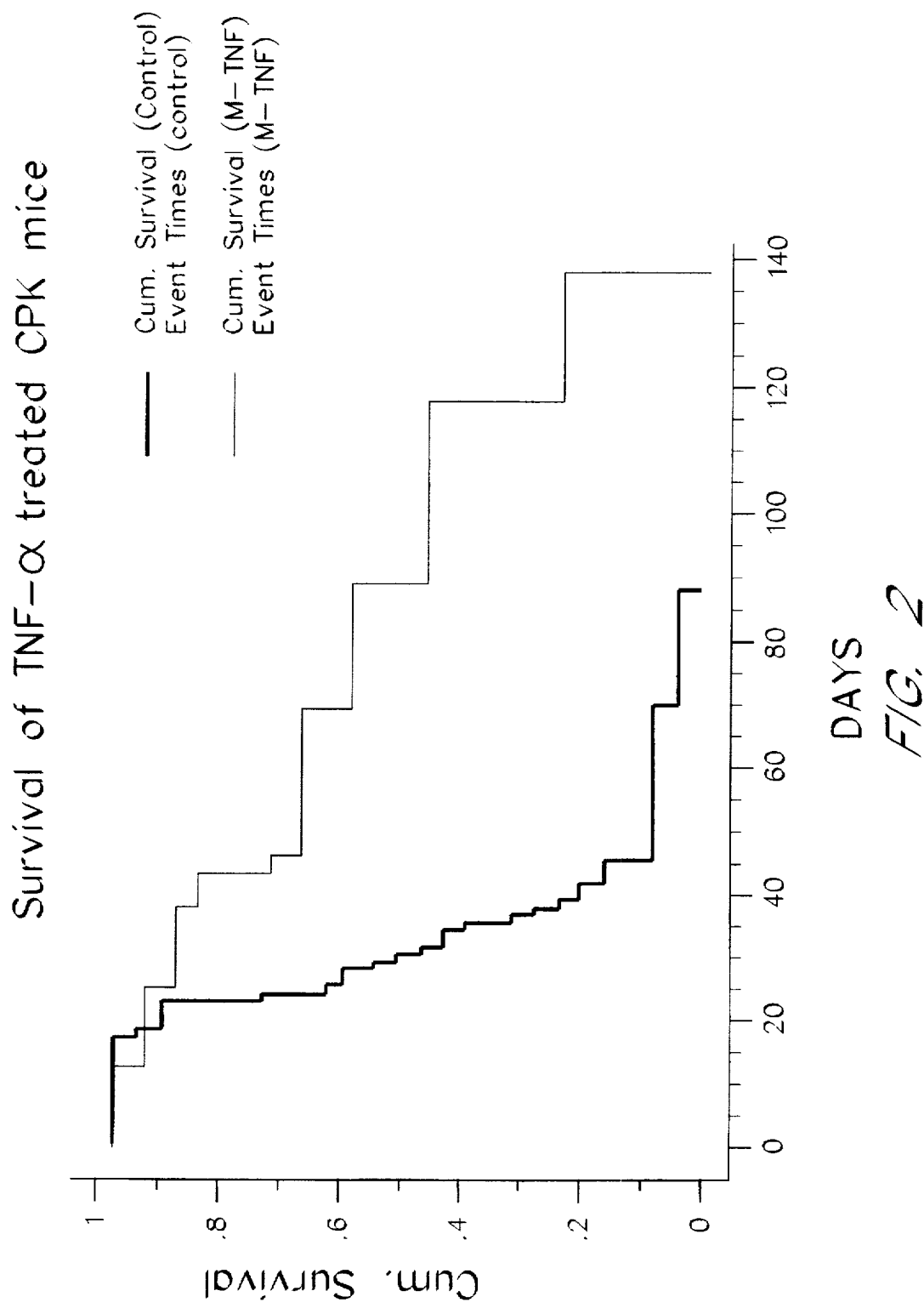
FIG. 2 shows the survival of TNF-α treated cpk mice. The number of days after TNF-α or placebo treatment is shown on the x-axis and the cumulative survival is shown on the y-axis.

All TNF-α experiments were initiated on day 7 by administering TNF-α to the entire litter. Despite treatment, the kidneys of polycystic cpk mice treated with TNF-α on day 7 continue to enlarge and become palpable by day 10. The kidneys of mice without palpably enlarged kidneys by day 10 were all histologically normal. FIG. 2 compares the survival of 21 polycystic cpk mice given 2 μg TNF-α every other day and 25 polycystic cpk mice treated similarly with saline. Over 90% of TNF-α treated polycystic cpk mice survived past 40 days of age. In contrast, only 20% of the saline treated cpk mice survived beyond 40 days of age. Almost 50% of TNF-α treated mice survived past 100 days of age. In contrast, none of the saline-treated mice lived past 90 days of age. Statistically, the difference in survival between control and TNF-α treated cpk mice is highly significant (Log-rank chi-square=24.17 and p<0.0001). Because taxol is known to stimulate TNF-α production, the ability of taxol to inhibit the progression of PKD in polycystic cpk mice is due, at lest in part, to this activity.

For histology studies, animals were sacrificed and their kidneys were fixed overnight in 10% neutral buffered formalin (Fisher Scientific, Pittsburgh, Pa.), dehydrated in ethanol, infiltrated and embedded in paraffin. Five micron histological sections were prepared and stained with periodic acid-Schiff stain, counter stained with hematoxylin and visualized by light microscopy.

A striking contrast was observed between the tightly packed functional nephrons seen within the histological sections of normal mice and the apoptotic loss of non-cystic nephrons in the kidneys of polycystic mice. Direct comparison between normal mice and polycystic mice at 10 days of age revealed a loss of approximately 50% of the non-cystic nephrons. Almost all of the remaining non-cystic nephrons were rapidly and completely lost during the next ten to fourteen days. By the third to fourth week after birth, only a few life sustaining neurons remained, during the three to four weeks of rapid progression to complete renal failure, no signs of tubular necrosis, interstitial inflammation or interstitial fibrosis were detected in the polycystic cpk kidneys.

Compared to kidneys obtained from a 28 day old azotemic polycystic cpk mouse, kidneys obtained from apparently healthy polycystic cpk mice treated with TNF-α for 90 days were significantly smaller in size. Kidneys from TNF-α treated polycystic cpk mice appeared to be very similar to kidneys from polycystic cpk mice treated weekly with taxol for the same length of time by both gross and histological criteria. Both of these treated kidneys had far fewer and much smaller cysts than kidneys from untreated or saline treated polycystic cpk mice. Histological examination revealed the presence of a number of hypertrophied nephrons in kidneys from both the TNF-α and taxol treated mice. Significant interstitial fibrosis was also observed in kidneys of both TNF-α and taxol treated mice. Both treated groups have kidneys with a large fluid filled central lumen which results from enlargement of the renal pelvis. This feature is most likely a result of the chronic renal disease state the treated mice experienced and not a result of the TNF-α or taxol treatment.

Renal function was assessed as described in the following example.

EXAMPLE 2

Determination of Renal Function

Mice were sacrificed at the indicated age and 0.5 ml blood was collected from the aorta. Serum creatinine was measured in triplicate using a commercial creatinine kit (Sigma, St. Louis, Mo.) with the following modifications. Because hemolysis of serum strongly interfered with the creatinine assay, hemoglobin in serum samples (100 μl) was precipitated with trichloroacetic acid at a final concentration of 10%. Precipitated proteins were removed by centrifugation at 13,000 rpm for 10 minutes and the serum neutralized to pH 7.0. Creatinine determination was preformed with 25 μl of the neutralized serum in flat-bottom rigid microtiter plates (Corning, Corning, N.Y.) according to the creatinine assay kit instructions, but scaled down to a 250 μl assay volume. Absorbance both before and after addition of the acid reagent was recorded at 490 nm using a Molecular Device VMax 96 well plate reader.

The average serum creatinine of three active polycystic mice treated with TNF-α was 3.3±0.6 mg/dl when they were sacrificed at 90 days of age.

Human cysts may be treated in vivo as described in the following example.

EXAMPLE 3

Treatment of Human Cysts

A subject having a cystic disease or at risk for developing a cystic disease is first identified. For example, a subject can be identified by a physician, who diagnoses that subject as having ADPKD. After identifying an appropriate subject for treatment, that subject is intravenously administered a pharmaceutically effective dose (e.g. 100,000 units/kg of recombinant human TNF-α. TNF-α can be administered either before a cyst has formed, in order to prevent its formation, or after a cyst has already been detected in a subject. This administration is repeated, for example, every three days during the time the patient has or is susceptible to developing a cyst. In this way an effective amount of the compound can be maintained in the subject.

It should be noted that the present invention is not limited to only those embodiments described in the Detailed Description. Any embodiment which retains the spirit of the present invention should be considered to be within its scope. However, the invention is only limited by the scope of the following claims.

What is claimed is:

1. A method for treating a mammal having a cystic disease, comprising the step of administering to said mammal a pharmacologically effective anti-cystic amount of TNF-α in a pharmacologically acceptable carrier, excipient or diluent.

2. The method of claim 1, wherein said mammal is a human.

3. The method of claim 1, wherein said cystic disease is selected from the group consisting of breast cysts, bronchogenic cysts, choledochal cysts, colloidal cysts, congenital cysts, dental cysts, epidermoid inclusions, hepatic cysts, hydatid cysts, lung cysts, mediastinal cysts, ovarian cysts, periapical cysts, pericardial cysts and polycystic kidney disease.

4. The method of claim 3, wherein said cystic disease comprises a polycystic kidney disease.

5. The method of claim 1, wherein said administering step is selected from the group consisting of intravenous, intraperitoneal, intraarterial, subcutaneous, oral and intramuscular administration.

6. The method of claim 5, wherein said administering step is intravenous.

* * * * *